(12) United States Patent
Rezai et al.

(10) Patent No.: US 7,833,174 B2
(45) Date of Patent: Nov. 16, 2010

(54) METHOD AND APPARATUS FOR SUBCUTANEOUSLY ADVANCING A DEVICE BETWEEN LOCATIONS

(75) Inventors: Ali R. Rezai, Bratenhal, OH (US); Ashwini D. Sharan, Mt. Laurel, NJ (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1100 days.

(21) Appl. No.: 10/502,611

(22) PCT Filed: Jan. 31, 2003

(86) PCT No.: PCT/US03/02991

§ 371 (c)(1),
(2), (4) Date: Apr. 4, 2005

(87) PCT Pub. No.: WO03/065874

PCT Pub. Date: Aug. 14, 2003

(65) Prior Publication Data

US 2005/0161052 A1 Jul. 28, 2005

Related U.S. Application Data

(60) Provisional application No. 60/353,695, filed on Feb. 1, 2002.

(51) Int. Cl.
*A61B 5/00* (2006.01)

(52) U.S. Cl. .................................................... 600/585

(58) Field of Classification Search .................. 600/585
See application file for complete search history.

(56) References Cited

U.S. PATENT DOCUMENTS

| 5,125,888 | A |   | 6/1992 | Howard et al. |
| 5,353,807 | A |   | 10/1994 | DeMarco |
| 5,431,640 | A | * | 7/1995 | Gabriel ........................ 604/270 |
| 5,931,818 | A | * | 8/1999 | Werp et al. ................... 604/270 |
| 6,126,647 | A | * | 10/2000 | Posey et al. .................. 604/270 |
| 6,157,853 | A |   | 12/2000 | Blume et al. |
| 6,216,026 | B1 |  | 4/2001 | Kuhn et al. |
| 6,216,030 | B1 |  | 4/2001 | Howard et al. |
| 6,226,547 | B1 |  | 5/2001 | Lockhart et al. |
| 6,475,223 | B1 |  | 11/2002 | Werp et al. |
| 2002/0019644 | A1 |  | 2/2002 | Hastings et al. |

* cited by examiner

*Primary Examiner*—Patricia C Mallari
(74) *Attorney, Agent, or Firm*—Tarolli, Sundheim, Covell & Tummino LLP

(57) ABSTRACT

A method and apparatus (10) for advancing a device (12) underneath the skin (102) in a mammalian body comprises a casing (50) made of a magnetic material. The casing (50) has a closed tip (64) at one end and an aperture (65) in an opposite end. The casing (50) includes an annular inner surface (70) that defines a cavity (76) within the casing for receiving a device (12) that projects through the aperture (65). The casing (50) further includes structure for attaching to the device (12). The casing (50) is operable to advance the device (12) through tissue (100) underlying the skin (102) in response to movement of a magnetic field across the skin.

20 Claims, 2 Drawing Sheets

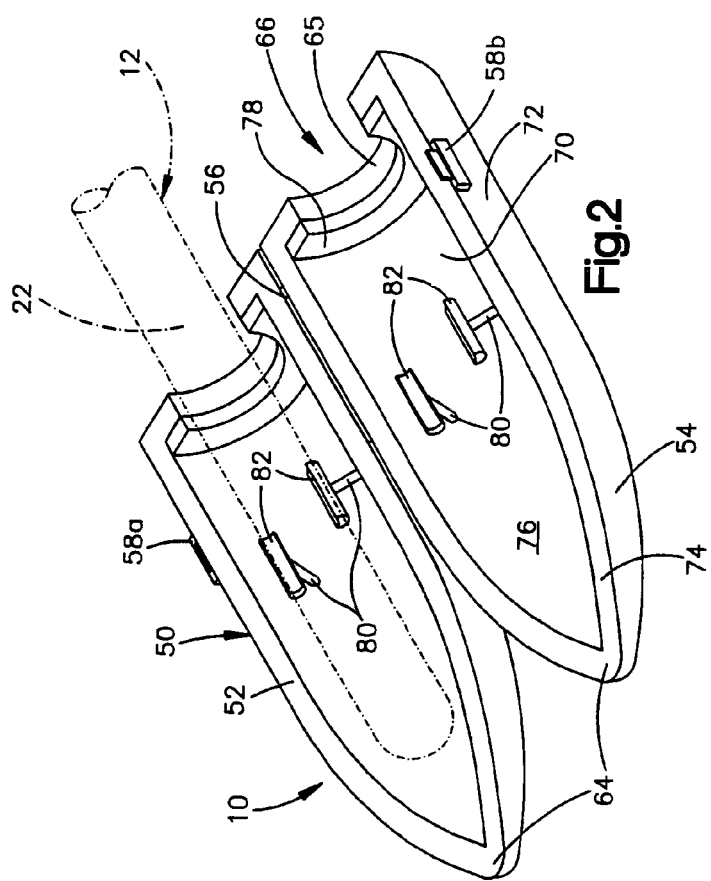
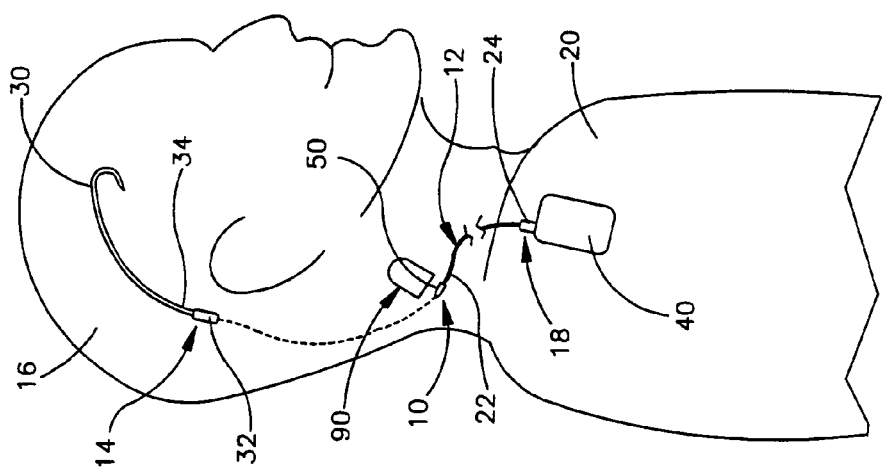

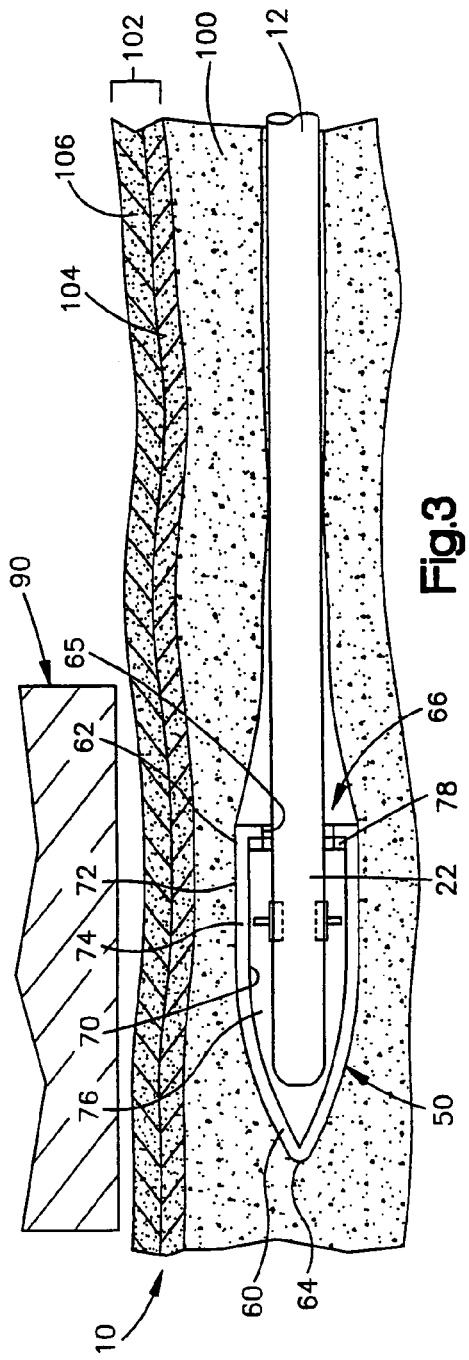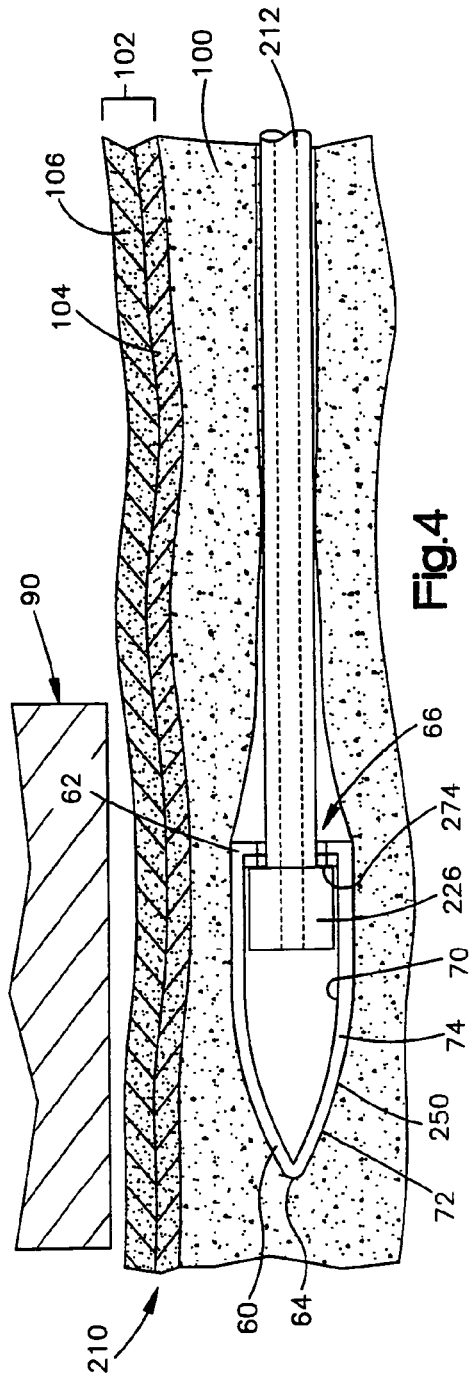

METHOD AND APPARATUS FOR SUBCUTANEOUSLY ADVANCING A DEVICE BETWEEN LOCATIONS

RELATED APPLICATIONS

This application claims the benefit of U.S. Provisional Patent Application Ser. No. 60/353,695, filed on Feb. 1, 2002.

FIELD OF THE INVENTION

The present invention relates to a method and apparatus for subcutaneously advancing a device between different locations in a mammalian body.

BACKGROUND OF THE INVENTION

An increasing number of patients with neurological disorders, such as epilepsy and Parkinson's disease, are undergoing surgery to implant devices for treating the disorders using techniques such as deep brain stimulation. The implanted devices can include an electrode that is implanted into the brain and/or a cerebrospinal fluid shunt implanted into the patient's head. The implanted devices can also include a stimulator device that is implanted into the patient's chest. The stimulator is then connected to the implanted electrode by an electrical lead that is run underneath the patient's skin (epidermis and dermis) between the patient's head and the patient's chest. The stimulator can be activated automatically or manually to electrically stimulate the brain via the implanted electrode and thereby curb or prevent seizures or other symptoms caused by neurological disorders. In the case of the cerebrospinal fluid shunt being implanted in the patient's head, it is often necessary to run a catheter underneath the patient's skin and connect the catheter to the implanted shunt.

One complication with the aforementioned surgical procedures and treatment methods is that the process of tunneling through the tissue under the skin to extend either a electrical lead or a catheter between the patient's head and chest can be quite time consuming and requires that the patient be under general anesthesia for a relatively long period of time. The tunneling process typically involves the use of a long tunneling rod to push/pull the electrical lead, or the catheter as the case may be, between the patient's head and chest. Such a tunneling rod can be hard to use and inaccurate at times. Hence, a need exists for a fast, simple, and accurate method and apparatus for subcutaneously advancing an electrical lead or a catheter between a patient's head and chest.

SUMMARY OF THE INVENTION

The present invention is an apparatus for advancing a device underneath the skin in a mammalian body. The apparatus comprises a casing made of a magnetic material. The casing has a closed tip at one end and an aperture in an opposite end. The casing includes an annular inner surface that defines a cavity within the casing for receiving a device that projects through the aperture. The casing further includes means for attaching to the device. The casing is operable to advance the device through tissue underlying the skin in response to movement of a magnetic field across the skin.

The present invention further includes an apparatus for subcutaneously advancing an elongated member between different locations in a mammalian body. The apparatus comprises a casing having a shape like a bullet and made of a magnetic material. The casing has oppositely disposed first and second ends. The first end is closed and forms a tip portion of the casing for tunneling through tissue underlying the skin. The second end is open to form a mouth portion of the casing. The casing includes annular inner and outer surfaces that extend between the first and seconds ends and which define a side wall portion of the casing. The inner surface further defines a cavity within the casing for receiving a distal end portion of the elongated member that projects through the mouth portion. The inner surface includes means for releasably connecting with the distal end portion of the elongated member. The casing is operable to advance the elongated member through the tissue underlying the skin between different locations in the body in response to movement of a magnetic field across the skin extending between the locations.

The present invention also provides a method for advancing a device underneath the skin in a mammalian body. According to the inventive method, a casing made of a magnetic material is provided. The casing has a closed tip at one end and connecting means for attaching to a device. The device is attached to the casing with the connecting means. The casing is inserted underneath the skin of a mammalian body in a first location. A magnetic field source is positioned over the casing. The magnetic field source is moved across the skin from the first location to a second location which causes the casing, and the device attached thereto, to correspondingly advance through the tissue underlying the skin to the second location.

The present invention further provides a method for subcutaneously advancing an elongated member between different locations in a mammalian body. According to this method, a casing having a shape like a bullet and made of a magnetic material is provided. The casing has oppositely disposed first and second ends. The first end is closed and forms a tip portion and the second end is open to form a mouth portion. The casing further includes annular inner and outer surfaces that extend between the first and seconds ends. The inner surface defines a cavity within the casing and includes means for releasably connecting with the distal end portion of the elongated member. The elongated member is inserted through the aperture in the casing and attached to the elongated member. The casing is inserted underneath the skin of a mammalian body in a first location. A magnetic field source is positioned over the casing. The magnetic field source is moved across the skin from the first location to a second location which causes the casing, and the elongated member attached thereto, to correspondingly advance through the tissue underlying the skin to the second location.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 1 is a schematic side view illustrating an apparatus for subcutaneously advancing a device between different locations within a mammalian body in accordance with the present invention;

FIG. 2 is a perspective view of the apparatus of FIG. 1 and shows the apparatus in a different condition;

FIG. 3 is a schematic sectional view of the apparatus of FIG. 1 as the apparatus being advanced subcutaneously; and FIG. 4 is a view similar to FIG. 3 illustrating an alternate embodiment of the present invention.

DESCRIPTION OF EMBODIMENTS

The present invention relates to a method and apparatus for subcutaneously advancing a device between different locations in a mammalian body. In accordance with a first embodiment of the present invention, FIG. 1 illustrates an apparatus 10 for subcutaneously advancing an electrical lead 12 between a first location 14 in a patient's head 16 and a second location 18 in the patient's chest 20. The electrical lead 12 is an elongated, insulated wire having oppositely disposed first and second ends 22 and 24.

As shown in FIG. 1, an electrode 30 for stimulating a patient's brain is implanted into the brain (not shown) through an incision (osteotomy) at the first location 14 in the patient's head 16 in a known manner. A first connector 32 for connecting with the first end 22 of the electrical lead 12 is disposed at a proximal end 34 of the electrode 30.

As is known in the art, a stimulator 40 is implanted into the patient's chest 20 through an incision (not shown) at the second location 16. The stimulator 40 includes means (not shown), such as electrical contacts or a receptacle, for connecting with the second end 24 of the electrical lead 12.

The apparatus 10 comprises a casing 50 made of a magnetic material, such as an appropriate stainless steel. The casing 50 has an outer diameter between 3 mm and 10 mm. As shown in FIG. 2, the casing 50 has a clamshell-type configuration formed by first and second body portions 52 and 54. The body portions 52 and 54 are connected by a hinge 56 and thus are movable relative to each other. The casing 50 includes a closure mechanism, schematically illustrated by reference numbers 58a and 58b, for securing the body portions 52 and 54 together.

Referring now to FIG. 3, the casing 50 has a shape like a bullet and includes oppositely disposed first and second ends 60 and 62. The first end 60 is closed and forms a tip portion 64 for tunneling through tissue underlying the patient's skin. The tip of the tip portion 64 has a semi-blunt shape which allows it to be sharp enough penetrate tissue, such as fascia, but which restricts the tip from poking out through the skin. The second end 62 of the casing 50 includes an aperture 65 that forms a mouth portion 66.

The casing 50 further includes annular inner and outer surfaces 70 and 72 that extend between the first and second ends 60 and 62 of the casing. The inner and outer surfaces 70 and 72 define a side wall portion 74 of the casing 50. Further, the inner surface 70 of the casing 50 defines a cavity 76 for receiving the first end 22 of the electrical lead 12. Inside the cavity 76, the casing 50 may also include a weighted flange 78 adjacent the mouth portion 66. The weighted flange 78 helps to keep the tip portion 64 of the casing 50 pointed straight ahead so the tip portion does not inadvertently poke through the skin.

A plurality of supports 80 extend radially inward into the cavity 76 from the inner surface 70 of the casing 50. The supports 80 are spaced circumferentially apart and each support includes an engagement pad 82 for engaging the first end 22 of the electrical lead 12.

The apparatus 10 further comprises a magnet 90 for providing a magnetic field that attracts the casing 50 and causes movement of the casing corresponding to movement of the magnet. The magnet 90 may be moved either manually or by a mechanism (not shown).

Following implantation of the stimulator 40 in the patient's chest 20, the second end 24 of the electrical lead 12 is connected to the stimulator. The electrical lead must now be run underneath the skin from the second location 18 in the patient's chest 20 to the first location 14 in the patient's head 16.

To subcutaneously advance the electrical lead 12 from the second location 18 to the first location 14, the first end 22 of the electrical lead is first connected to the casing 50. The first and second body portions 52 and 54 of the casing 50 are spread apart and the first end 22 is placed into the cavity 76 with the remainder of the lead 12 projecting out of the casing 50 through the aperture 65. When the body portions 52 and 54 of the casing 50 are brought together and secured to one another by the closure mechanism 58a and 58b, the engagement pads 82 in the cavity 76 press against the first end 22 of the electrical lead 12 with an interference fit that secures the casing to the electrical lead.

Next, the casing 50, with the electrical lead 12 attached, is inserted underneath the patient's skin in the second location 18. More specifically, the casing 50 is inserted into the fascia layer 100 just below the skin 102, which consists of a dermis layer 104 and an epidermis layer 106, as shown schematically in FIG. 3.

The magnet 90 is then positioned directly over the casing 50 outside of the skin 102 so that the casing is attracted by the magnetic field of the magnet. The magnet 90 is then moved across the skin 102 from the second location 18 toward the first location 14. This movement of the magnet 90 causes the casing 50, as well as the electrical lead 12 attached thereto, to correspondingly advance through the fascia layer 100 toward the first location 14 as shown schematically in FIG. 3. Continued movement of the magnet 90 allows the casing 50 to tunnel its way between the two locations, taking the electrical lead 12 along with it, as shown schematically by the dashed line in FIG. 1.

When the casing 50 reaches the first location 14 in the patient's head 16, the casing is disconnected from the first end 22 of the electrical lead 12 by opening the closure mechanism 58a and 58b on the casing. The first end 22 of the electrical lead 12 can then be connected to the connector 32 on the end of the electrode 30 so that the stimulator 40 is operatively coupled with the electrode and treatment of the neurological disorder can begin.

Using the apparatus 10 as described above reduces the amount of time required to tunnel the electrical lead 12 between the first and second locations 14 and 18, and thereby reduces the length of time that the patient is kept under general anesthesia. The method and apparatus 10 described above provides a simple and accurate way to complete the tunneling process with lower risk of pneomothorax and inadvertent skin penetration that the conventional tunneling rod technique. Additionally, the apparatus 10 can lower the chances of infection by tunneling drains at a farther site from the incision, as it has been shown that longer tunnel lengths result in less infections.

FIG. 4 illustrates an apparatus 210 in accordance with an alternate embodiment of the present invention. In FIG. 4, parts of the apparatus 210 that are identical to parts of the apparatus 10 described above are identified by the same reference numbers.

The embodiment shown in FIG. 4 illustrates how the present invention is adaptable for use in advancing a catheter 212, used in connection with an implanted cerebrospinal fluid shunt (not shown), under the patient's skin 102. The catheter 212 has a first end 222 that includes a connector 226.

The apparatus 210 comprises a magnetic casing 250 that is nearly identical to the casing 50 previously described, but does not include any structure projecting into the cavity 76 in the casing for engaging the catheter 212 or the connector 226. Rather, the casing 250 is secured to the catheter 212 by capturing the connector 226 inside the cavity 76. A portion 274 of the inner surface 70 at the second end 62 of the casing 250 engages the connector 226 and keeps the catheter 212 from moving axially relative to the casing.

The apparatus 210 functions like the apparatus 10 to enable the subcutaneous advancement of the catheter 212 from the second location 18 to the first location 14 through corresponding movement of the magnet 90. Consequently, the apparatus 210 enjoys all of the same benefits and advantages as are described above for the apparatus 10.

It should be understood to those skilled in the art that the present invention may be applied to achieve subcutaneous advancement of many types of devices and should not be limited to electrical leads and catheters. Further, it should also be appreciated that the devices disclosed herein can be advanced subcutaneously from any starting location to any ending location and should not be limited to tunneling from a patient's chest to a patient's head or vice versa.

From the above description of the invention, those skilled in the art will perceive improvements, changes and modifications. Such improvements, changes and modifications within the skill of the art are intended to be covered by the appended claims.

Having described the invention, we claim:

1. An apparatus for advancing a device underneath the skin in a mammalian body, said apparatus comprising:
    a casing comprising at least two body portions that are movable relative to each other, said casing made entirely of a magnetic material, said casing having a closed tip at one end and an aperture in an opposite end;
    said casing including an annular inner surface that defines a cavity within said casing for receiving a device that projects through said aperture;
    said casing further including means for attaching to the device;
    said casing being operable to advance the device through tissue underlying the skin in response to movement of a magnetic field across the skin.

2. The apparatus of claim 1 wherein said device comprises an electrical lead.

3. The apparatus of claim 1 wherein said device comprises a shunt catheter.

4. The apparatus of claim 1 further comprising a magnet for providing a magnetic field that is movable across the skin to cause corresponding subcutaneous movement of said casing.

5. The apparatus of claim 1 wherein said at least two body portions of said casing are connected to each other by a hinge.

6. An apparatus for advancing a device underneath the skin in a mammalian body, said apparatus comprising:
    a casing made entirely of a magnetic material, said casing having a closed tip at one end and an aperture in an opposite end;
    said casing including an annular inner surface that defines a cavity within said casing for receiving a device that projects through said aperture;
    said casing further including means for attaching to the device that include at least one support extending from said inner surface of said casing;
    said casing being operable to advance the device through tissue underlying the skin in response to movement of a magnetic field across the skin.

7. The apparatus of claim 6 wherein said at least one support includes an engagement pad for pressing against the device with an interference fit.

8. The apparatus of claim 1 wherein said means for attaching to the device includes a portion of said inner surface.

9. The apparatus of claim 6 wherein said means for attaching to the device includes a plurality of supports extending from said inner surface of said casing.

10. An apparatus for subcutaneously advancing an elongated member between different locations in a mammalian body, said apparatus comprising:
    a casing comprising at least two body portions that are movable relative to each other, said casing made entirely of a magnetic material, said casing having oppositely disposed first and second ends, said first end being closed and forming a tip portion of said casing for tunneling through tissue underlying the skin, said second end being open to form a mouth portion of said casing;
    said casing including annular inner and outer surfaces that extend between said first and second ends and which define a side wall portion of said casing, said inner surface further defining a cavity within said casing for receiving a distal end portion of the elongated member that projects through said mouth portion;
    said inner surface including means for releasably connecting with the distal end portion of the elongated member;
    said casing being operable to advance an elongated member through the tissue underlying the skin between different locations in the body in response to movement of a magnetic field across the skin extending between the locations.

11. The apparatus of claim 10 wherein said elongated member comprises an electrical lead.

12. The apparatus of claim 10 wherein said elongated member comprises a shunt catheter.

13. The apparatus of claim 10 wherein said first end of said casing includes a semi-blunt tip.

14. The apparatus of claim 10 wherein second end of said casing includes a weighted flange.

15. The apparatus of claim 10 wherein said means for releasably connecting to the elongated member includes a portion of said inner surface.

16. The apparatus of claim 10 wherein said at least two body portions of said casing are connected to each other by a hinge.

17. The apparatus of claim 10 further comprising a magnet for providing a magnetic field that is movable across the skin to cause corresponding subcutaneous movement of said casing.

18. An apparatus for subcutaneously advancing an elongated member between different locations in a mammalian body, said apparatus comprising:
    a casing made entirely of a magnetic material, said casing having oppositely disposed first and second ends, said first end being closed and forming a tip portion of said casing for tunneling through tissue underlying the skin, said second end being open to form a mouth portion of said casing;
    said casing including annular inner and outer surfaces that extend between said first and second ends and which define a side wall portion of said casing, said inner surface further defining a cavity within said casing for receiving a distal end portion of the elongated member that projects through said mouth portion;
    said inner surface including means for releasably connecting with the distal end portion of the elongated member that include at least one support extending from said inner surface of said casing;
    said casing being operable to advance an elongated member through the tissue underlying the skin between different locations in the body in response to movement of a magnetic field across the skin extending between the locations.

19. The apparatus of claim 18 wherein said at least one support includes an engagement pad for pressing against the elongated member with an interference fit.

20. The apparatus of claim 18 wherein said means for attaching to the device includes a plurality of supports extending from said inner surface of said casing.

* * * * *